United States Patent [19]

Council

[11] 4,280,493
[45] Jul. 28, 1981

[54] NOSE SHIELD

[76] Inventor: Edward L. Council, 4161 McClellan, Detroit, Mich. 48214

[21] Appl. No.: 85,390

[22] Filed: Jan. 30, 1980

[51] Int. Cl.³ .......................................... A61M 15/08
[52] U.S. Cl. .............................. 128/207.18; 128/139; 128/342; 128/206.11; 128/201.18
[58] Field of Search ............ 128/201.18, 139, 203.22, 128/206.11, 207.18, 342, 250, 151, 152, 200.24, 207.28, 221, 235, 238, 239, 241, 242, 251, 252, 253

[56] References Cited

U.S. PATENT DOCUMENTS

| 890,990 | 6/1908 | MacDonald | 128/241 |
|---|---|---|---|
| 1,429,546 | 9/1922 | Stokes | 128/203.22 |
| 1,839,606 | 1/1932 | Simmons | 128/342 |
| 2,335,936 | 12/1943 | Hanlon | 128/207.18 X |
| 2,693,799 | 11/1954 | Herman, Jr. | 128/201.18 |
| 3,424,152 | 1/1969 | Kuhlman | 128/139 X |

*Primary Examiner*—Henry J. Recla
*Attorney, Agent, or Firm*—Cullen, Sloman, Cantor, Grauer, Scott & Rutherford

[57] ABSTRACT

The nose shield is adapted to be located in and to conform to the lining of the nostril of the nose so as to shield the nasal passage or passages from wind or air currents which bring discomfort to some persons. The nose shield is effective to prevent air containing oxygen required for a person to breathe from entering the nasal passages of the nose. It further is effective to direct such air to the air passage leading to the back of the mouth and throat for breathing purposes thus by-passing the nasal passages and eliminating discomfort caused by air or wind entering the nasal passage. The nose shield comprises a unitary thin wall generally bowl shaped body opened at one end and closed at the other end. The side wall of the body engages the lining of the nostril. The open end faces outwardly of the nostril. In one embodiment, the closed end of the body has a centrally located opening through which air may enter the air passage leading to the back of the mouth. In the preferred embodiment an air delivery tube is mounted in the opening and is secured to the closed end of the body for directing and delivering air to such air passage. A nose shield is placed in each nostril of the person requiring protection from wind or air currents.

7 Claims, 3 Drawing Figures

NOSE SHIELD

BACKGROUND OF THE INVENTION

When the small blood vessels in a person's nose swell as a result, as an example, of cold air entering the nose, such swelling creates a sticky liquid called mucus which brings discomfort. It has been necessary in the past to treat same medically by using an appropriate decongestant which breaks up the mucus whereby a person can then blow his or her nose to eliminate same thereby permitting such person to breathe normally.

The present invention is a mechanical shield which fits into a person's nostril so as to yield the nasal passages and to permit air to be directed more readily to the air passage leading to the back of the mouth and throat for breathing purposes.

SUMMARY OF THE INVENTION

It is a feature of the present invention to provide a nose shield for each nostril of the nose and which is hidden from view when inserted in the nostril and which generally conforms to the inside lining of the nostril.

It is a further feature of the present invention to provide a nose shield which is effective to prevent air containing oxygen required for a person to breathe from entering the nasal passage or passages of the nose thereby minimizing or reducing congestion in the nose.

It is a still further feature of the present invention to provide a nose shield which is effective to direct air received within the nostril to the air passage leading to the back of the mouth for breathing purposes thus bypassing the nasal passages and eliminating or minimizing the congestion of the nose.

Another feature of the present invention is to provide a nose shield comprising a unitary, thin wall, generally bowl or funnel shaped body opened at one end and closed at the other end, with the body wall engaging the lining of the nostril and having the open end thereof located so as to face outwardly of the nostril.

Still another feature of the present invention is to provide a nose shield of the aforementioned type wherein the closed end of the body has a centrally located opening therein which forms an orifice through which air from the nostril is directed into the air passage leading to the back of the person's mouth and throat, with the remaining part of the body shielding the nasal passages from air.

Still another feature of the present invention is to provide a nose shield of the aforementioned type wherein an air delivery tube is mounted in the opening and is secured to the closed end of the body for delivering air to the person's air passage, mouth and throat.

A further feature of the present invention is to provide a nose shield of the aforementioned type wherein the delivery tube has first and second tubular sections, with the first section extending rearwardly of the closed end away from the body and the second section extending forwardly of the closed end and terminating inside of the body. With such a construction the delivery tube at the end thereof within the body is adapted to receive the air entering the nostril and to direct and deliver same therethrough to the other end thereof located near the person's air passage leading to the back of the mouth and throat.

Another feature of the present invention is to provide a nose shield of the aforementioned type wherein the closed end of the body is dome shaped, with the remaining wall being generally cylindrical.

Still another feature of the present invention is to provide a nose shield of the aforementioned type wherein the body has a longitudinal axis, with the cylindrical wall of the body adjacent the open end thereof forming an annular surface or edge which is inclined with respect to such axis. A resilient rim is located adjacent the inclined edge for the purpose of assisting in holding the nose shield in the nostril.

A further feature of the present invention is to provide a nose shield of the aforementioned type wherein the body and delivery tube are made from a plastic material, such material being flexible and/or soft so as to minimize any discomfort to the user.

A still further feature of the present invention is to provide a nose shield of the aforementioned type wherein the tube has a length of approximately $\frac{3}{4}''$ to $1''$, with the first section having a length of approximately $3/16''$ to $\frac{1}{2}''$.

Another feature of the present invention is to provide a nose shield of the aforementioned type wherein the thin wall, bowl shaped body has a uniform thickness in the range of $1/32''$ to $3/32''$.

Still another feature of the present invention is to provide a non-medical, non-prescription nose shield which minimizes congestion in a person's nose and assists in directing air to the person's air passage leading to the back of the mouth and throat.

Finally, it is a feature of the present invention to provide a nose shield which is economical to manufacture, easy to place in the nostril and to remove therefrom and is easy to clean and to maintain to protect a person's health.

PREFERRED EMBODIMENT OF THE INVENTION

Figure 1:
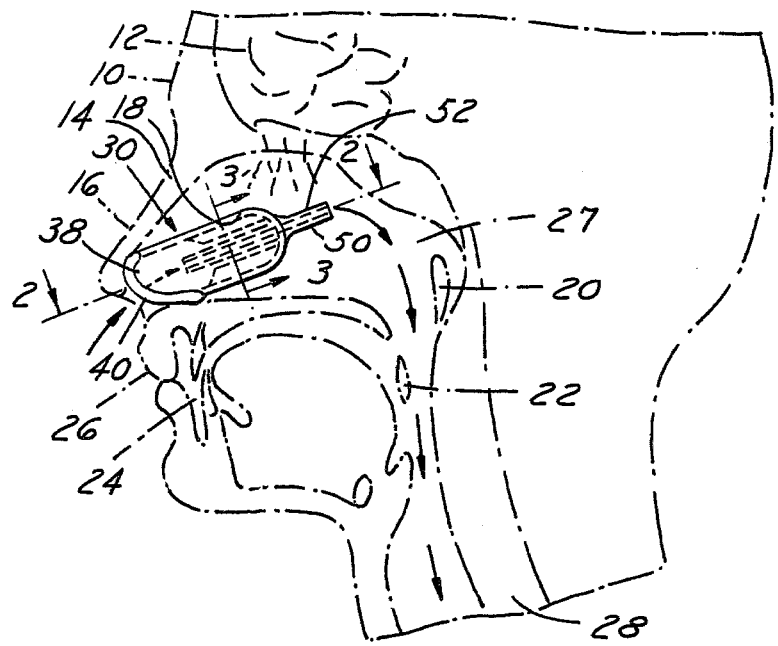
FIG. 1 is a fragmentary pictorial illustration of a person's head illustrating the nose shields inserted in the nostrils.

Many persons take breathing for granted and are generally not bothered with any problem which brings him or her discomfort when breathing.

When a person breathes in it is to supply the blood with fresh oxygen which enables the cells to produce energy. When the person breathes waste carbon dioxide is ejected which the blood has carried away from the cells. Also when you breathe out you are helping your body to keep cool by expelling a little water vapor. However, such can be done in other ways such as by perspiring, for example. So the really important work which a person does when he or she breathes is exchanging carbon dioxide for oxygen.

It is generally known that there are two ways in which you can breathe. When you are sitting comfortably in a chair reading you are hardly aware that you are breathing at all but you are breathing very lightly through your nose at about sixteen times a minute. If you were to drop this book though and run around the block at top speed you might soon find yourself huffing.

By this rapid breathing through the mouth you provide your blood with the extra oxygen required when you use a lot of energy in a short time.

A person's mouth is not really designed for breathing as will readily be discovered on very cold days. Then you keep your mouth tightly closed because you can feel the coldness of the air. Even your teeth feel the cold. On extremely cold days you lower your chin so that your mouth is protected by a coat collar or scarf. The reason is that the cold air passing through the mouth does not have a chance to become warmed and the cold air actually causes a shock to the lungs.

However, a person can breathe quite comfortably through the nose even though the nose may feel cold on the outside. This is because inside the nose there are a great many small blood vessels which swell with blood when the air is cold. As the air passes the blood vessels on its way to the lungs it is warmed to body temperature. However, there is one slight disadvantage to this when the small blood vessels swell they cause more of a sticky liquid called mucus to be produced in the nose. That is why on a cold morning a person has to blow his or her nose so often. The same effect is caused by a cold in the head. Mucus moistens and protects the delicate tissue which lines all of the air passages which are referred to herein as the nasal passages. Along with the hairs in the nostrils, the tissue in the nose traps particals of dust preventing the dust from reaching the lungs.

For some persons such air passages or the nasal passages are aggravated by air normally entering the nose. Such person or persons finds themselves continually congested in the nose resulting in discomfort. Such nasal congestion can be treated medically or with various decongestants now on the market.

The present invention provides a non-medical, non-prescription mechanical nose shield which shields the air from the nasal passage or passages and directs the air to the air passages leading from the nose to the back of the mouth or to the throat.

Referring now to FIG. 1 is illustrated diagramatically a person's head 10 containing the usual brain 12, septum 14, nose 16, nostrils 18, adenoids 20, tonsils 22, mouth 24 and lips 26. The nostrils 18 have the usual linings or tissues containing blood vessels and air or nasal passages, not shown. Leading away from each nostril 18 is an air passage 27 which leads to the back of the mouth 24 and to the throat 28. Each nostril 18 contains a nose shield 30.

The nose shield 30 comprises a unitary body, cup or funnel like element 32 closed at one end 34 and opened at the other end 36. The body 32 is made from a generally flexible plastic material which is non-injurious to the lining of the nostril.

Figure 2:
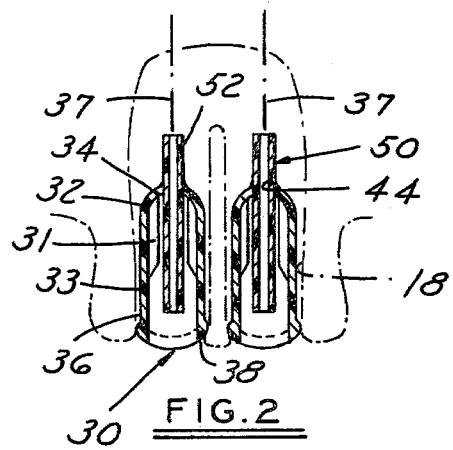
FIG. 2 is a sectional full size view through the nose shields located in the nostrils taken generally on the line 2—2 of FIG. 1.
Figure 3:
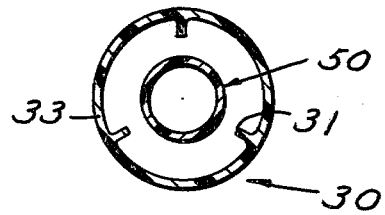
FIG. 3 is an enlarged sectional view through one of the nose shields taken on the line 3—3 of FIG. 1.

The body 32 at the closed end 34 is of dome shape or rounded, with the remaining part or wall of the body 32 formed by a generally cylindrical wall portion 33. The inside of the body has reinforcing ribs 31 extending from the closed end 34 toward the other end as shown in FIG. 2.

The opened end 36 of the cylindrical wall portion 33 is formed by a generally annular surface or edge 38 which is inclined or slanted or sloped with respect to the longitudinal body axis 37 so as to conform generally to the configuration of the nostril 18 as best shown in FIG. 1. When inserted in the nostril 18, the shield 30 is generally hidden from normal viewing. It is held in the nostril 18 by means of an annular resilient rim or ring 40 which is located adjacent the edge 38. The rim 40 may be made from rubber or other soft resilient material which is not injurious to the lining of the nostril.

The closed end 34 of the body 32 has an orifice which is generally centrally located with respect to the axis 37. The cylindrical wall portion 33 of the body 32 surrounds or closes the nasal passages to wind and air. Air entering the nostril 18, in one embodiment of the invention, passes through the orifice or opening 44 and is directed through the air passage 27 towards the back of the mouth and throat.

The body 32 is made from a plastic material which is soft or flexible so as not to damage or injure the nostril. It is made by molding or other suitable techniques and has a generally uniform thickness in the range of 1/32" to 3/34". The body 32 is shaped like a sewing thimble except for the small opening or orifice 44 in the closed end thereof and for the slanted or inclined edge 38 which is designed to assist in contouring the body to the nose or nostril.

In the preferred embodiment an elongated tube 50 of approximately ¾" to 1" in length, an outside diameter of approximately ⅛", an inside diameter of approximately 3/64" to 5/64", and made from a flexible or soft plastic material is located in the orifice or opening 44 and is secured to the body 32 by a commercially available cement. The tube 50 has a pair of sections 52, 54 with the first section 52 extending rearwardly towards the back of the mouth and throat. The first section 52 has a length of approximately 3/16" to ½". The second section 54 has a length which terminates within the body 32 as illustrated in FIG. 2. The tube 50 forms an air delivery and directional conduit for taking the air entering the nostril 18 and diverting same to the air passage 27.

With the aforesaid construction the side wall 33 of the shield 30 overlies or shields the blood vessels and nasal passages in the nostril from wind and air currents received in the nostril. The leading end of the delivery tube 50 located in the body 32 picks up and transmits the air through tube 50 to the person's air passage 27 for breathing purposes. When installed in the nostril, the shield 30 is retained therein due in part to the resilient rim 40 and is hidden from normal viewing. The nostrils are thereby shielded from the wind and air currents when a pair of shields 30 are properly fitted and installed.

The shields 30 may have different lengths and shapes to accommodate persons of various ages, sizes and shapes.

I claim:

1. A nose shield including nasal insert means adapted to be located in and to sealingly conform to the lining of the nostril of the nose, effective to prevent air containing oxygen required for a person to breathe from entering the nasal passages of the nose and further effective to direct such air to a person's air passage leading from the nostril to the back of the mouth and to the throat for breathing purposes thus by-passing the nasal passages, said nasal insert means comprising a unitary, thin wall, generally bowl shaped body made from a flexible plastic material and having a longitudinal axis, opened at one end and closed at the other end, with the closed end being of dome shape and adapted to conform to and contact the lining of the nostril adjacent the air passage, with the side wall of the body being of generally cylindrical configuration and located adjacent said open end of said body, said side wall of the body adapted to engage the lining of the nostril and with the open end of the body turned outwardly from within the nostril, a relatively small opening provided in the closed dome shape end of said body through which air entering the nostril is directed towards the air passage, mouth and throat for breathing purposes, said axis extending through said opening, an air delivery tube made from a flexible plastic material mounted in said opening and secured to said closed end of said body for delivering air to the person's air passage and throat, said air delivery tube having first and second tubular sections, said first section extending rearwardly of said closed dome shape end away from said body and adapted to be received in said air passage and said second section extending forwardly of said closed dome shape end and terminating inside of said body, said air delivery tube at the end thereof terminating within said body adapted to receive air entering the nostril and directing and delivering same therethrough to the other end thereof adapted to be located in the air passage.

2. The nose shield defined in claim 1, wherein said cylindrical wall adjacent said open end of said body forms an edge of generally annular configuration, said edge being inclined with respect to the longitudinal axis of said body.

3. The nose shield defined in claim 2, wherein said body adjacent said inclined annular edge is provided with a resilient rim which is adapted to fit snugly in the entrance to the nostril to retain the shield therein.

4. The nose shield defined in claim 1, wherein said delivery tube has a length of approximately ¾" to 1".

5. The nose shield defined in claim 1, wherein said first section has a length of approximately 3/16" to ½".

6. The nose shield defined in claim 1, wherein said thin wall body has a uniform thickness in the range of 1/32" to 3/32".

7. The nose shield defined in claim 1, wherein said delivery tube has an inside diameter of approximately 3/64" to 5/64".

* * * * *